US010383545B2

(12) United States Patent
Cho et al.

(10) Patent No.: US 10,383,545 B2
(45) Date of Patent: Aug. 20, 2019

(54) APPARATUS AND METHOD FOR DETERMINING BIO-INFORMATION OF TARGET USING IMPULSE RADAR

(71) Applicant: Daegu Gyeongbuk Institute of Science and Technology, Daegu (KR)

(72) Inventors: Hui Sup Cho, Daegu (KR); Young Jin Park, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 415 days.

(21) Appl. No.: 15/362,873

(22) Filed: Nov. 29, 2016

(65) Prior Publication Data

US 2018/0085013 A1    Mar. 29, 2018

(30) Foreign Application Priority Data

Sep. 29, 2016 (KR) .................. 10-2016-0125691
Oct. 4, 2016 (KR) .................. 10-2016-0127798

(51) Int. Cl.
*A61B 5/024* (2006.01)
*G01S 13/02* (2006.01)
*G01S 13/88* (2006.01)
*A61B 5/00* (2006.01)
*A61B 5/08* (2006.01)
(Continued)

(52) U.S. Cl.
CPC .......... *A61B 5/0816* (2013.01); *A61B 5/024* (2013.01); *A61B 5/0507* (2013.01); *A61B 5/7207* (2013.01); *G01S 13/0209* (2013.01); *G01S 13/53* (2013.01); *G01S 13/88* (2013.01); *A61B 5/725* (2013.01)

(58) Field of Classification Search
CPC ..... A61B 5/024; A61B 5/0507; A61B 5/0816; A61B 5/7207; A61B 5/725; G01S 13/0209; G01S 13/53; G01S 13/88
See application file for complete search history.

(56) References Cited

U.S. PATENT DOCUMENTS

2013/0006124 A1* 1/2013 Eyal .................. A61B 5/024
                                                    600/483
2018/0035916 A1* 2/2018 Hirose ................. A61B 5/113

FOREIGN PATENT DOCUMENTS

KR    1020080047699    5/2008
KR    1020110008080    1/2011
KR      101070326     10/2011

* cited by examiner

Primary Examiner — Michael T Rozanski
(74) Attorney, Agent, or Firm — Hodgson Russ LLP

(57) ABSTRACT

An apparatus and method for determining bio-information of a target using an impulse radar are provided. The method may include generating a frame set by accumulating frames received at preset time intervals, determining a first magnitude spectrum of the frame set corresponding to a first frequency axis by performing a frequency conversion of frames included in the frame set in a sampler index axis direction, determining a second magnitude spectrum of the frame set corresponding to the first frequency axis and a second frequency axis by performing a frequency conversion of the first magnitude spectrum in a time axis direction, determining a third magnitude spectrum of the frame set by adding up values of the second magnitude spectrum for each second frequency, and determining a frequency indicating a peak in the third magnitude spectrum as a heartbeat frequency of the target.

2 Claims, 12 Drawing Sheets

(51) Int. Cl.
    *G01S 13/53*     (2006.01)
    *A61B 5/05*     (2006.01)

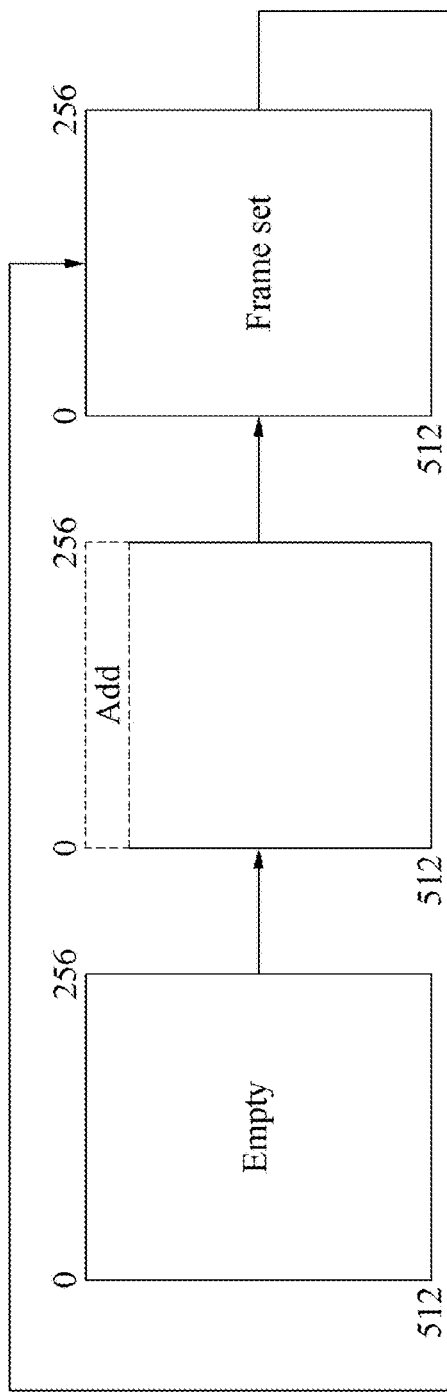
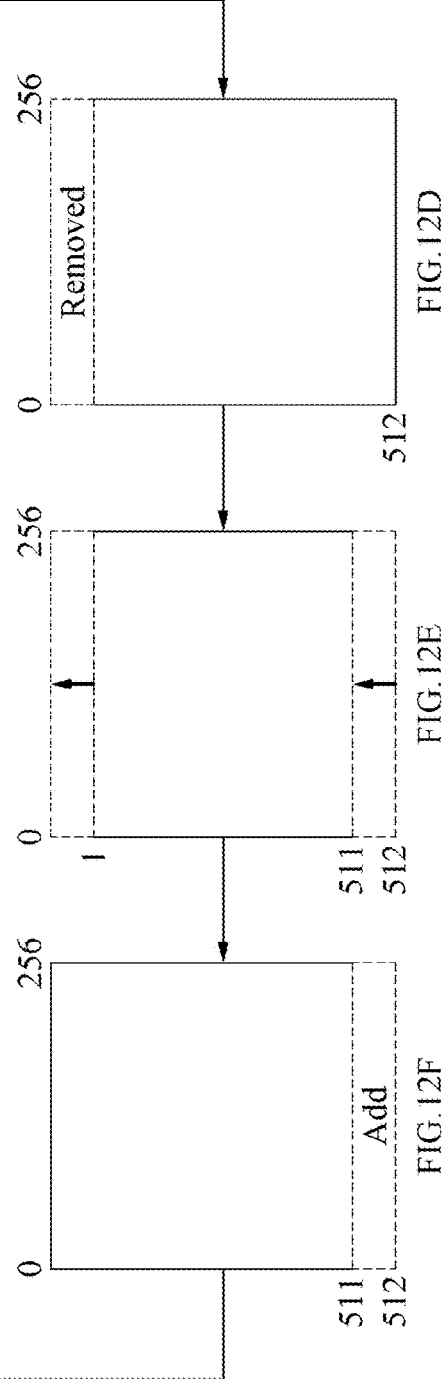

APPARATUS AND METHOD FOR DETERMINING BIO-INFORMATION OF TARGET USING IMPULSE RADAR

CROSS-REFERENCE TO RELATED APPLICATION(S)

This application claims the priority benefit of Korean Patent Application No. 10-2016-0125691 filed on Sep. 29, 2016, Korean Patent Application No. 10-2016-0127798 filed on Oct. 4, 2016, and Korean Patent Application No. 10-2016-0127819 filed on Oct. 4, 2016, in the Korean Intellectual Property Office, the disclosures of which are incorporated herein by reference for all purposes.

BACKGROUND

1. Field of the Invention

One or more example embodiments relate to an apparatus and method for determining bio-information of a target using an impulse radar, and more particularly, relate to an apparatus and method for determining bio-information of a target by performing a frequency conversion of a single frame derived by radar pulses reflected from the target, by converting data to frequency domain data and by applying an additional process.

2. Description of the Related Art

Radar technologies have been used to detect a target at a long distance or to measure a distance to a target in an aviation field and a military field. Recently, an attempt has been made to acquire bio-information, for example, a pulse, a heartbeat or a respiration from a person located at a close distance using radar technologies.

For example, an impulse radar technology and a continuous wave (CW) Doppler radar technology may be used as a radar technology for acquiring bio-information of humans. The above two radar technologies are different from each other in a power consumption, a target detection distance and a spatial resolution, and accordingly may be applied to different application fields.

Among the above radar technologies, an ultra wideband (UWB) impulse radar technology has an advantage of a low power consumption and low risk of overexposure to electromagnetic waves when the UWB impulse radar is used for humans. Also, the UWB impulse radar technology has an excellent characteristic of coexistence with neighboring devices, and is regarded as an appropriate scheme to acquire bio-information of a person due to a relatively high spatial resolution in comparison to other schemes.

However, when a UWB impulse radar is used to acquire bio-information of a person, the UWB impulse radar is vulnerable to a sudden and unintended movement of a target. Due to a motion artifact caused by the sudden and unintended movement, information about a heartbeat and a respiration may be distorted or lost. Accordingly, there is a desire to solve the above issue.

SUMMARY

Example embodiments may provide an apparatus and method for determining bio-information of a target by performing a frequency conversion of a single frame derived by radar pulses reflected from the target, by converting data to frequency domain data and by applying an additional process.

Example embodiments may also provide an apparatus and method for robustly extracting bio-information of a target by removing a frame with a transition portion in which a transition occurs due to a movement of the target among a plurality of frames derived by radar pulses reflected from the target and by minimizing an influence of an unintended movement of the target.

According to an aspect, there is provided a method of determining bio-information of a target, the method including generating a frame set by accumulating frames received at preset time intervals, the frames being generated by overlapping of radar pulses reflected from a target of which a heart rate is to be measured, determining a first magnitude spectrum of the frame set corresponding to a first frequency axis by performing a frequency conversion of frames included in the frame set in a sampler index axis direction, determining a second magnitude spectrum of the frame set corresponding to the first frequency axis and a second frequency axis by performing a frequency conversion of the first magnitude spectrum in a time axis direction, determining a third magnitude spectrum of the frame set by adding up values of the second magnitude spectrum for each second frequency, and determining a frequency indicating a peak in the third magnitude spectrum as a heartbeat frequency of the target.

The method may further include filtering the first magnitude spectrum in the time axis direction using a band-pass filter (BPF) with a frequency band corresponding to the heartbeat frequency, and applying a window function corresponding to a data length in the time axis direction to the filtered first magnitude spectrum. The determining of the second magnitude spectrum may include determining the second magnitude spectrum by performing a frequency conversion of the first magnitude spectrum, to which the window function is applied, in the time axis direction.

According to another aspect, there is provided a method of determining bio-information of a target, the method including generating a frame set by accumulating frames received at preset time intervals, the frames being generated by overlapping of radar pulses reflected from a target of which a heart rate is to be measured, removing a transition portion in which a transition occurs due to a movement of the target from the generated frame set, and determining a heartbeat frequency of the target based on the frame set from which the transition portion is removed, wherein the radar pulses correspond to a radar signal that reflects the movement of the target.

The removing of the transition portion may include extracting first sampler indices, each indicating a maximum peak of each of frames included in the frame set, determining a sampler index corresponding to a largest number of maximum peaks among the first sampler indices as a second sampler index used as a criterion to generate a movement profile, generating a movement profile based on the movement of the target using a difference between a first sampler index and a second sampler index, and aligning the frames based on the movement profile.

The aligning of the frames may include controlling a maximum peak of each of the frames to match a maximum peak indicated by second sampler index based on the movement profile, and removing a frame with the transition portion from the frame set.

The determining of the heartbeat frequency may include applying a Lomb-Scargle periodogram to extract a periodic component based on the frame set from which the transition portion is removed.

According to another aspect, there is provided a method of determining bio-information of a target, the method including generating a frame set by accumulating frames received at preset time intervals, the frames being generated by overlapping of radar pulses reflected from a target of which a heart rate is to be measured, determining a magnitude spectrum of the frame set corresponding to a frequency axis by performing a frequency conversion of frames included in the frame set in a sampler index axis direction, removing a portion corresponding to a movement of the target from the magnitude spectrum, and determining a heartbeat frequency of the target based on the magnitude spectrum from which the portion corresponding to the movement of the target is removed, wherein the radar pulses correspond to a radar signal that reflects the movement of the target.

The removing of the portion corresponding to the movement of the target may include extracting first sampler indices, each indicating a maximum peak of each of the frames in the frame set, determining a sampler index corresponding to a largest number of maximum peaks among the first sampler indices as a second sampler index used as a criterion to generate a movement profile, generating a movement profile based on the movement of the target using a difference between a first sampler index and a second sampler index, and removing the portion corresponding to the movement of the target based on the generated movement profile.

The determining of the heartbeat frequency may include applying a Lomb-Scargle periodogram to extract a periodic component based on the magnitude spectrum.

According to another aspect, there is provided a method of determining bio-information of a target, the method including generating a frame set by accumulating frames received at preset time intervals, the frames being generated by overlapping of radar pulses reflected from a target of which a respiratory rate is to be measured, determining a magnitude spectrum of the frame set corresponding to a frequency axis by performing a frequency conversion of frames included in the frame set in a sampler index axis direction, and determining the respiratory rate of the target based on the magnitude spectrum. The method may further include filtering the magnitude spectrum using a low-pass filter (LPF) to remove a ripple component of a high frequency band corresponding to a heartbeat frequency of the target from the magnitude spectrum. The determining of the respiratory rate may include determining the respiratory rate based on the filtered magnitude spectrum.

The determining of the respiratory rate may include calculating an average peak of the magnitude spectrum by adding up values of the filtered magnitude spectrum for each frequency, and determining the respiratory rate based on a period derived by the calculated average peak and based on a respiratory frequency of the target determined based on the derived period.

According to another aspect, there is provided an apparatus for determining bio-information of a target, the apparatus including a processor configured to perform signal processing of frames generated by overlapping of radar pulses reflected from a target of which a heart rate is to be measured. The processor may be configured to generate a frame set by accumulating frames received at preset time intervals, to determine a first magnitude spectrum of the frame set corresponding to a first frequency axis by performing a frequency conversion of frames included in the frame set in a sampler index axis direction, to determine a second magnitude spectrum of the frame set corresponding to the first frequency axis and a second frequency axis by performing a frequency conversion of the first magnitude spectrum in a time axis direction, to determine a third magnitude spectrum of the frame set by adding up values of the second magnitude spectrum for each second frequency, and to determine a frequency indicating a peak in the third magnitude spectrum as a heartbeat frequency of the target.

The processor may be further configured to filter the first magnitude spectrum in the time axis direction using a band-pass filter (BPF) with a frequency band corresponding to the heartbeat frequency, and to apply a window function corresponding to a data length in the time axis direction to the filtered first magnitude spectrum. The processor may be further configured to determine the second magnitude spectrum by performing a frequency conversion of the first magnitude spectrum, to which the window function is applied, in the time axis direction.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIGS. 12A, 12B, 12C, 12D, 12E and 12F are diagrams illustrating a process of generating a frame set according to an example embodiment.

DETAILED DESCRIPTION

Figure 1:
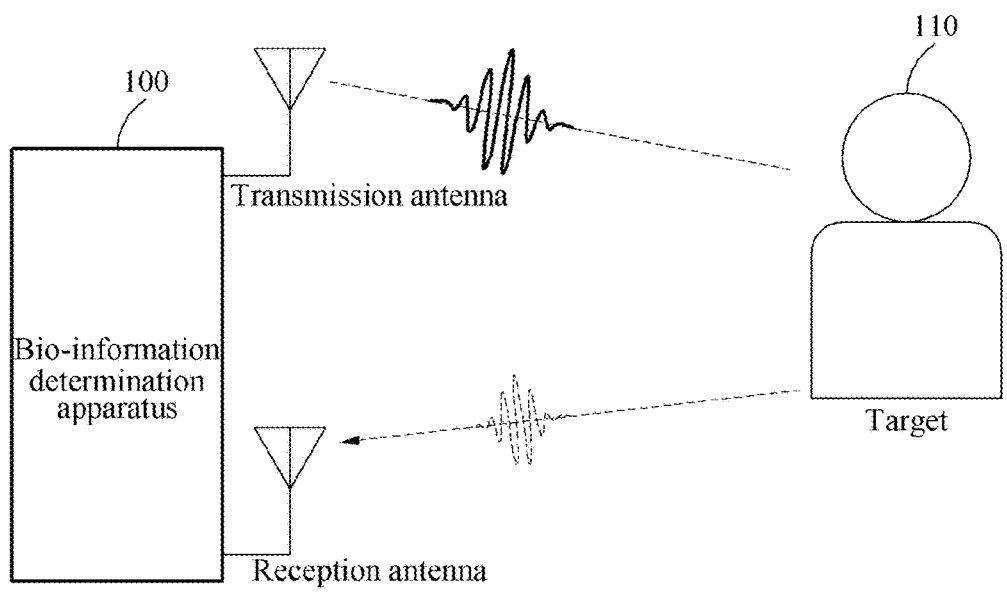
FIG. 1 is a diagram illustrating a system for determining a heartbeat frequency of a target using an impulse radar according to an example embodiment.

Particular structural or functional descriptions of example embodiments according to the concept of the present disclosure disclosed in the present disclosure are merely intended for the purpose of describing the example embodiments and the example embodiments may be implemented in various forms and should not be construed as being limited to those described in the present disclosure.

Though example embodiments according to the concept of the present disclosure may be variously modified and be several example embodiments, specific example embodiments will be shown in drawings and be explained in detail. However, the example embodiments are not meant to be limited, but it is intended that various modifications, equivalents, and alternatives are also covered within the scope of the claims.

Although terms of "first," "second," etc. are used to explain various components, the components are not limited to such terms. These terms are used only to distinguish one component from another component. For example, a first component may be referred to as a second component, or similarly, the second component may be referred to as the first component within the scope of the right according to the concept of the present disclosure.

When it is mentioned that one component is "connected" or "coupled" to another component, it may be understood that the one component is directly connected or coupled to another component or that still other component is interposed between the two components. Also, when it is mentioned that one component is "directly connected" or "directly coupled" to another component, it may be understood that no component is interposed therebetween. Expressions used to describe the relationship between components should be interpreted in a like fashion, for example, "between" versus "directly between," or "adjacent to" versus "directly adjacent to."

The terminology used herein is for the purpose of describing particular example embodiments only and is not intended to be limiting of example embodiments. As used herein, the singular forms are intended to include the plural forms as well, unless the context clearly indicates otherwise. It will be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Hereinafter, example embodiments will be described in detail with reference to the accompanying drawings. The scope of the right, however, should not be construed as limited to the example embodiments set forth herein. Regarding the reference numerals assigned to the elements in the drawings, it should be noted that the same elements will be designated by the same reference numerals.

FIG. 1 is a diagram illustrating a system for determining a heartbeat frequency of a target using an impulse radar according to an example embodiment.

To determine a heartbeat frequency of a target 110, a bio-information determination apparatus 100 may project a transmission radar signal toward the target 110 using a transmission antenna. The transmission radar signal projected using the transmission antenna may be, for example, a pulse type radar signal. For example, the transmission radar signal may be an ultra wideband (UWB) impulse type radar signal that is less harmful to humans and that consumes low power. A UWB impulse type radar signal projected by the bio-information determination apparatus 100 may have a frequency characteristic, for example, a central frequency and a bandwidth, that is set as a standard.

The bio-information determination apparatus 100 may determine the heartbeat frequency of the target 110 based on a reception radar signal. The reception radar signal may be collected using a reception antenna by reflecting the projected transmission radar signal from the target 110.

In a related art, a method of determining a heartbeat frequency of a target using a reception radar signal is provided. However, when the target slightly moves due to a respiration, it is difficult to determine an exact heartbeat frequency.

Even though a distance between the target 110 and a radar antenna changes because the target 110 slightly moves, the bio-information determination apparatus 100 may minimize an influence of a change in the distance and may determine the heartbeat frequency of the target 110.

Figure 2A:
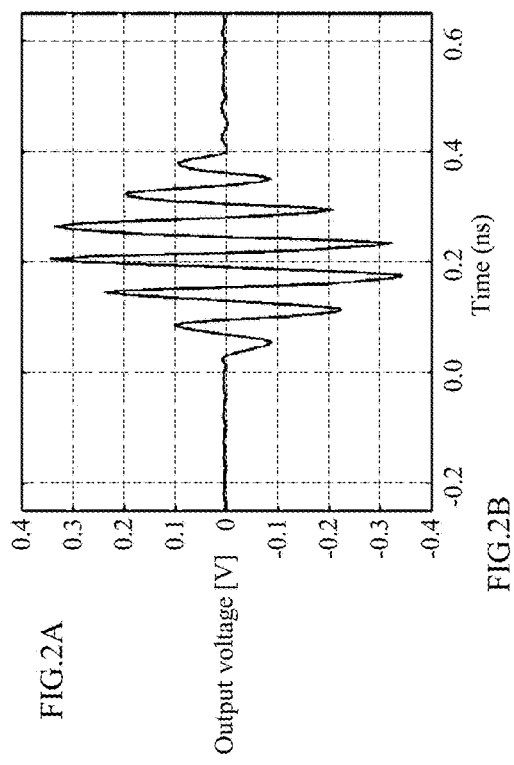
FIGS. 2A, 2B and 2C are diagrams illustrating a method of generating a frame set according to an example embodiment.
Figure 2C:
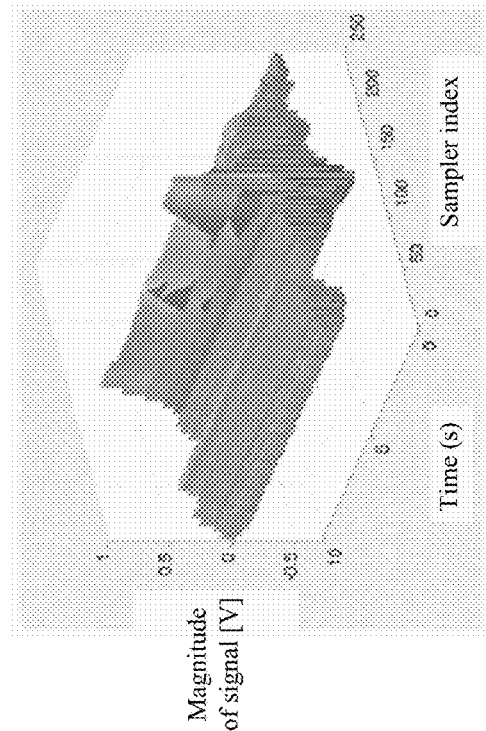
Figure 2B:
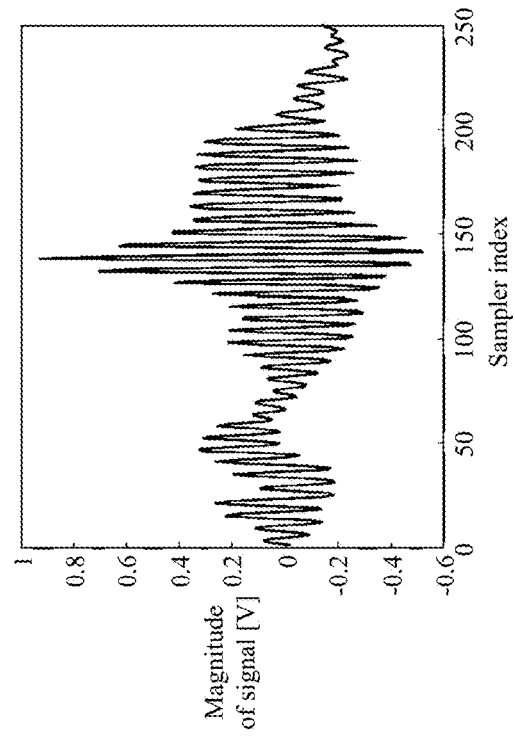

FIGS. 2A, 2B and 2C illustrate a method of generating a frame set according to an example embodiment.

In FIG. 2A, a transmission radar signal projected by the bio-information determination apparatus 100 of FIG. 1 may be a pulse type signal with an extremely narrow width in a time axis. The bio-information determination apparatus 100 may project the transmission radar signal toward a target at regular intervals using a transmission antenna. The bio-information determination apparatus 100 may collect a reception radar signal using a reception antenna by reflecting the projected transmission radar signal from the target. The bio-information determination apparatus 100 may collect reception radar signals using the reception antenna at preset time intervals. The reception radar signal collected using the reception antenna may be a signal with multiple overlapping radar pulses.

The bio-information determination apparatus 100 may convert the collected reception radar signal to digital data. For example, the collected reception radar signal may be sampled using a plurality of samplers and may be converted to the digital data. In the present disclosure, the reception radar signal converted to the digital data may be referred to as a "frame."

FIG. 2B illustrates a form of a single frame. In FIG. 2B, a sampler index axis corresponding to a horizontal axis represents a sampler index number, and a signal magnitude axis corresponding to a vertical axis represents a voltage of a radar signal collected using the reception antenna. Each sampler index number may be proportional to a distance between a target and a radar antenna. For example, when the sampler index number increases, the distance between the target and the radar antenna may increase.

To efficiently extract the heartbeat frequency of the target 110 from the reception radar signal, the bio-information determination apparatus 100 may generate a frame set by accumulating a plurality of frames over time, and may use the frame set. A number of accumulated frames may be a number of the form 2n, for example, 512 or 1024.

FIG. 2C illustrates a form of a frame set. The frame set may have a form in which a magnitude of a reception radar signal is expressed on a plane formed by a sampler index axis and a time axis. For example, the frame set may be represented as a data structure for a two-dimensional (3D) matrix.

For example, the bio-information determination apparatus 100 may support "256" samplers. In this example, "256" sampler indices of a frame set may be formed. Also, the bio-information determination apparatus 100 may collect "512" reception radar signals at each time interval of 20 milliseconds (ms). Frames collected at each time interval of 20 ms may be accumulated in a time axis direction to form a frame set. Thus, the time axis may have "512" units of time (0.02 second (s)), and a single frame set may be generated based on reception radar signals collected for 10.24 s. However, there is no limitation to the example, and thus numerical values of the frame set may vary depending on needs and uses.

The frame set generated by the bio-information determination apparatus 100 may include bio-information of the target 110. For example, data indicating a largest fluctuation among data in a time axis direction in the frame set may correspond to information about a respiration of the target 110. As shown in FIG. 2C, a largest fluctuation of data in the time axis direction corresponding to a $138^{th}$ sampler may indicate that a phase of a reception radar signal fluctuates over time due to the respiration of the target 110.

Unlike the largest fluctuation, relatively small ripples shown in data in the time axis direction corresponding to almost all samplers may represent information about a heartbeat of the target 110. The bio-information determination apparatus 100 may extract the information about the heartbeat and the respiration of the target 110 by processing the data in the time axis direction in a time domain or a frequency domain.

Figure 3:
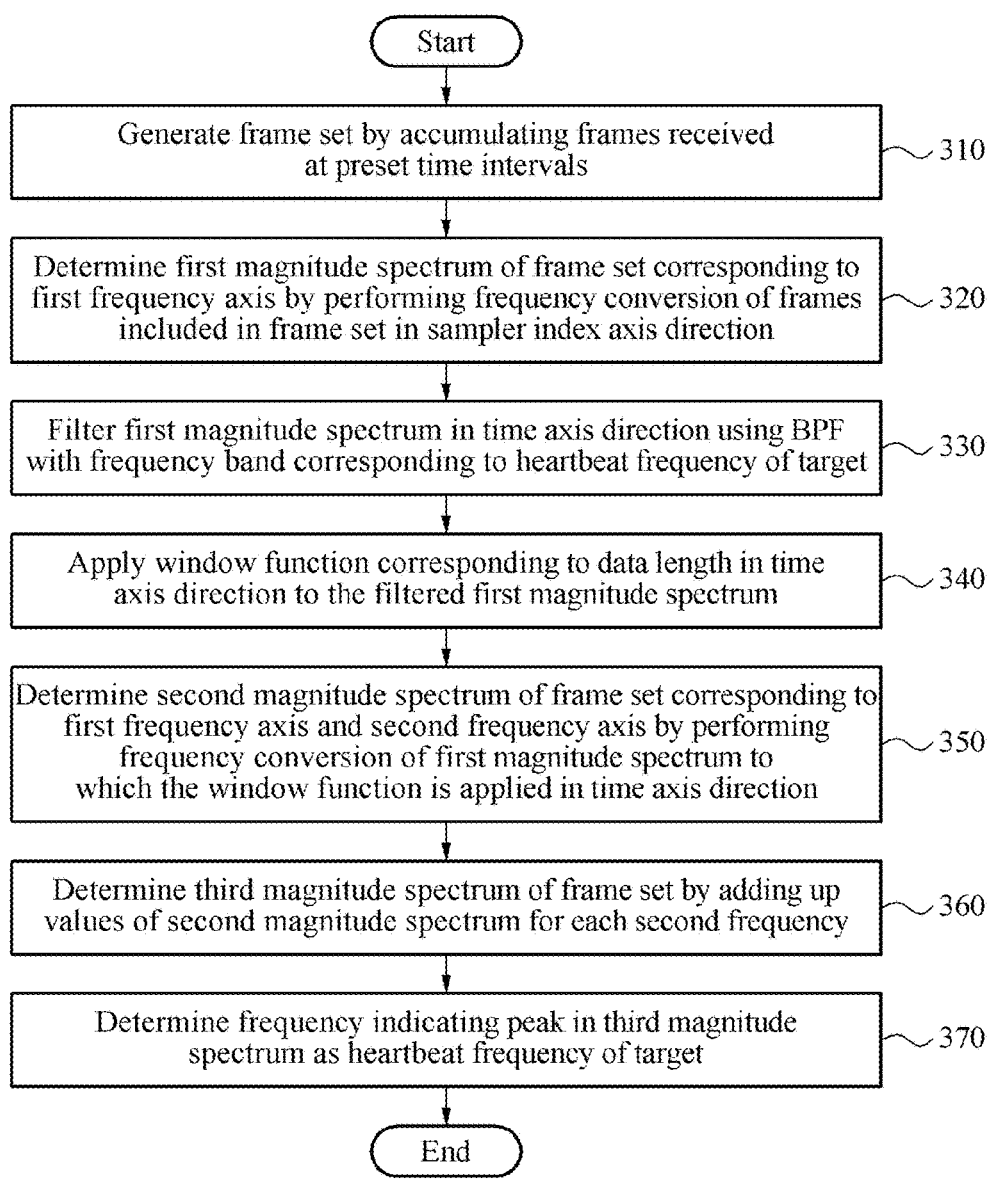
FIG. 3 is a flowchart illustrating an example of a method of determining a heartbeat frequency of a target using an impulse radar according to an example embodiment.

FIG. 3 is a flowchart illustrating an example of a method of determining a heartbeat frequency of a target using an impulse radar according to an example embodiment. The method of FIG. 3 may be performed by the bio-information determination apparatus 100 of FIG. 1.

Referring to FIG. 3, in operation 310, the bio-information determination apparatus 100 may generate a frame set by accumulating frames received at preset time intervals. The frames may be generated by overlapping of radar pulses reflected from a target of which a heart rate is to be measured.

The generated frame set may have a form in which a magnitude of a reception radar signal is expressed on a plane formed by a sampler index axis and a time axis. For example, the frame set may be represented as a data structure for a 2D matrix.

In operation 320, the bio-information determination apparatus 100 may determine a first magnitude spectrum of the frame set corresponding to a first frequency axis by performing a frequency conversion of frames included in the frame set in a sampler index axis direction.

In the related art, a frame set is generated by accumulating a plurality of frames, and a frequency conversion is performed on data in a time axis direction corresponding to a specific sampler, for example, a sampler corresponding to a peak, to extract a respiratory frequency or a heartbeat frequency of a target. However, because a position of a sampler corresponding to a maximum peak occurring in each of frames included in the frame set fluctuates in response to a change in a distance between the target and a radar antenna, there is a need to attempt to perform a frequency conversion while continuing to track the fluctuation in the position, which may cause an inconvenience.

For example, a maximum peak occurring in each of the frames in the frame set may frequently fluctuate in a sampler index axis direction due to an influence by a respiration, and the like. Thus, it may be difficult to extract a respiratory frequency or a heartbeat frequency of a target based on data in the time axis direction corresponding to a specific sampler.

Figure 4A:
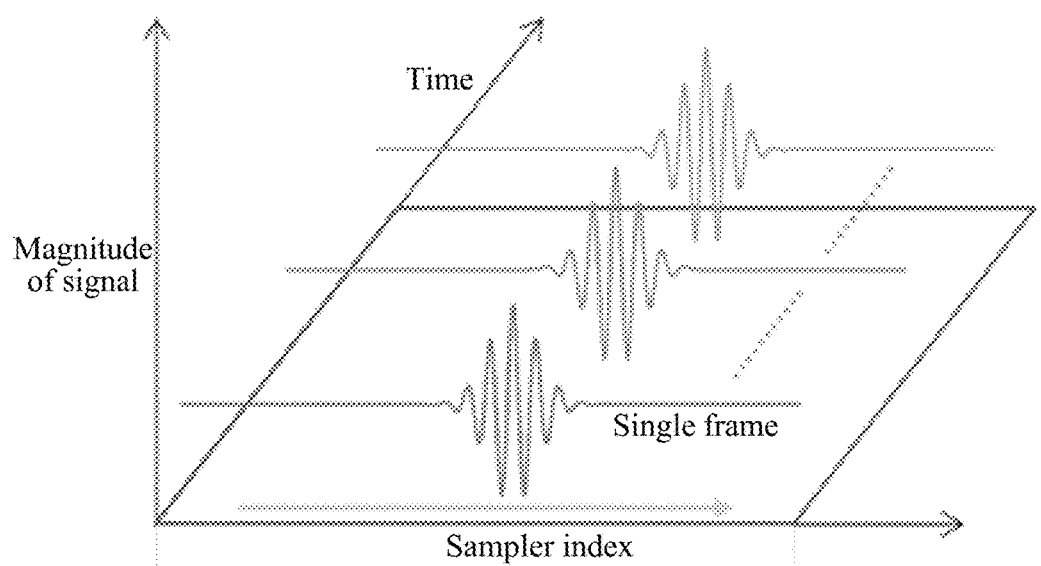
FIGS. 4A and 4B are diagrams illustrating a method of performing a frequency conversion of a frame set in a sampler index axis direction according to an example embodiment.
Figure 4B:
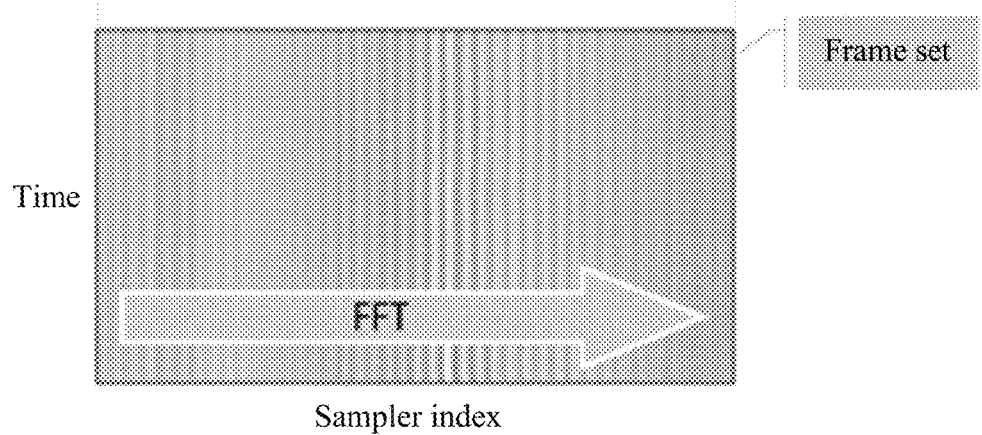

To overcome the above limitation, the bio-information determination apparatus 100 may perform a frequency conversion of each of frames included in a frame set of FIG. 4A in a sampler index axis direction as shown in FIG. 4B. As a result, a sampler index axis of the frame set may be converted to a first frequency axis, and the first magnitude spectrum of the frame set corresponding to the first frequency axis may be determined. For example, the bio-information determination apparatus 100 may use a fast Fourier transform (1-1-T) to perform a frequency conversion of each of the frames.

The frequency conversion may be performed as described above, because even though the target slightly moves in the sampler index axis direction, an influence of a slight movement of the target may be reduced in the frequency domain.

In the first magnitude spectrum determined by performing the frequency conversion of each of the frames, the reception radar signal may have a highest basic frequency, and an influence of a phase fluctuation in the reception radar signal due to a heartbeat or a respiration of the target may be represented in a form of a change over time in a size of a main lobe and a size of a side lobe for a basic frequency of the reception radar signal. The bio-information determination apparatus 100 may extract the heartbeat frequency of the target using the above fluctuation component of the first magnitude spectrum.

In operation 330, the bio-information determination apparatus 100 may filter the first magnitude spectrum in a time axis direction using a band-pass filter (BPF) with a frequency band corresponding to the heartbeat frequency.

A reception radar signal collected by the bio-information determination apparatus 100 using a reception antenna may include noise or information about the respiration as well as information about the heartbeat of the target. Thus, to more accurately determine the heartbeat frequency of the target, the bio-information determination apparatus 100 may need to filter the first magnitude spectrum to acquire the information about the heartbeat of the target.

Figure 5A:
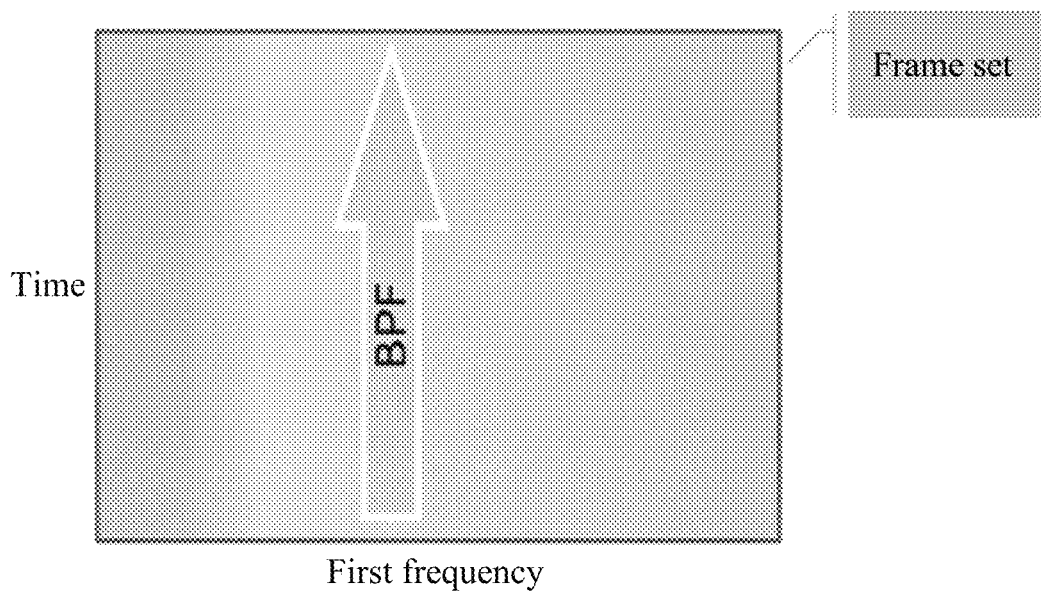
FIGS. 5A and 5B are diagrams illustrating a method of performing, in a time axis direction, a frequency conversion of a first magnitude spectrum determined by performing a frequency conversion of a frame set according to an example embodiment.

To this end, the bio-information determination apparatus 100 may filter the first magnitude spectrum in a time axis direction using the BPF with the frequency band corresponding to the heartbeat frequency, as shown in FIG. 5A. The BPF may be used to pass frequencies of 1 hertz (Hz) to 3 Hz corresponding to a heartbeat frequency of a human. In the first magnitude spectrum filtered using the BPF, a fluctuation component caused by the heartbeat of the target may remain.

In operation 340, the bio-information determination apparatus 100 may apply a window function corresponding to a data length in the time axis direction to the filtered first magnitude spectrum.

For example, the bio-information determination apparatus 100 may multiply the window function by data in the time axis direction for each first frequency included in the filtered first magnitude spectrum, to reduce a spectral leakage in a next frequency conversion.

In this example, the window function may have the same length as a length of an original signal, and may have a shape in which the original signal starts from "0" to smoothly increase to "1" and "1" maintained in an end portion of the original signal smoothly decreases to "0." For example, the bio-information determination apparatus 100 may multiply the window function by data in the time axis direction for each first frequency, to obtain a result of a continuous wave without a steep gradient.

In operation 350, the bio-information determination apparatus 100 may determine a second magnitude spectrum of the frame set corresponding to the first frequency axis and a second frequency axis by performing a frequency conversion of the first magnitude spectrum, to which the window function is applied, in the time axis direction.

Figure 5B:
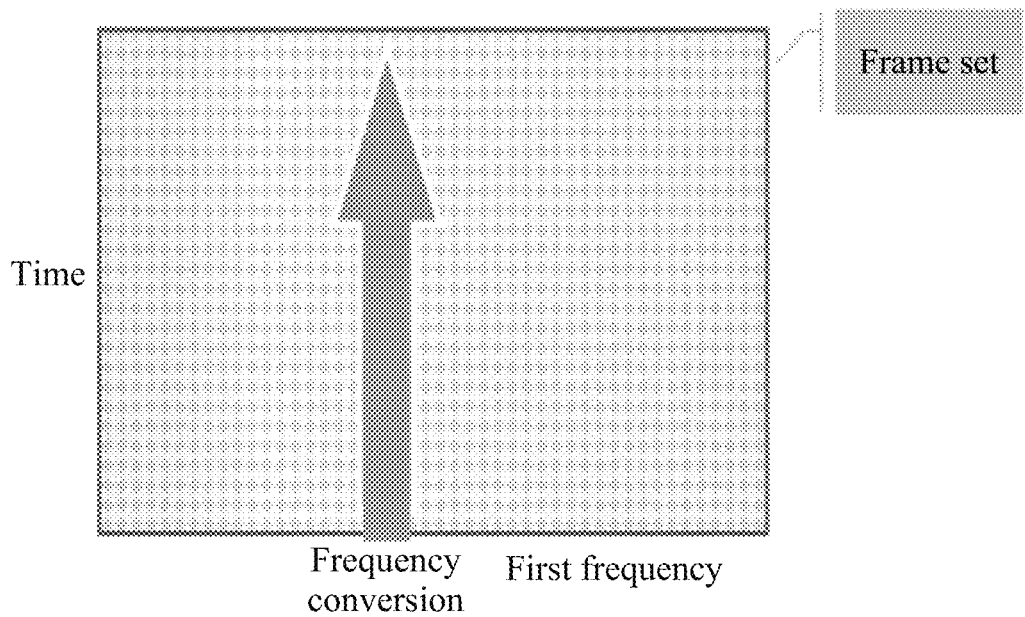

For example, the bio-information determination apparatus 100 may perform a frequency conversion of the first magnitude spectrum, to which the window function is applied, in a time axis direction, as shown in FIG. 5B. In this example, a time axis of the first magnitude spectrum may be converted to the second frequency axis, and the second magnitude spectrum corresponding to the first frequency axis and the second frequency axis may be determined. Similarly, the bio-information determination apparatus 100 may use the FFT to perform the frequency conversion of the first magnitude spectrum, and may extract a frequency corresponding to a fluctuation component in the time axis direction caused by an influence on the heartbeat of the target.

In operation 360, the bio-information determination apparatus 100 may determine a third magnitude spectrum of the frame set by adding up values of the second magnitude spectrum for each second frequency.

Figure 6A:
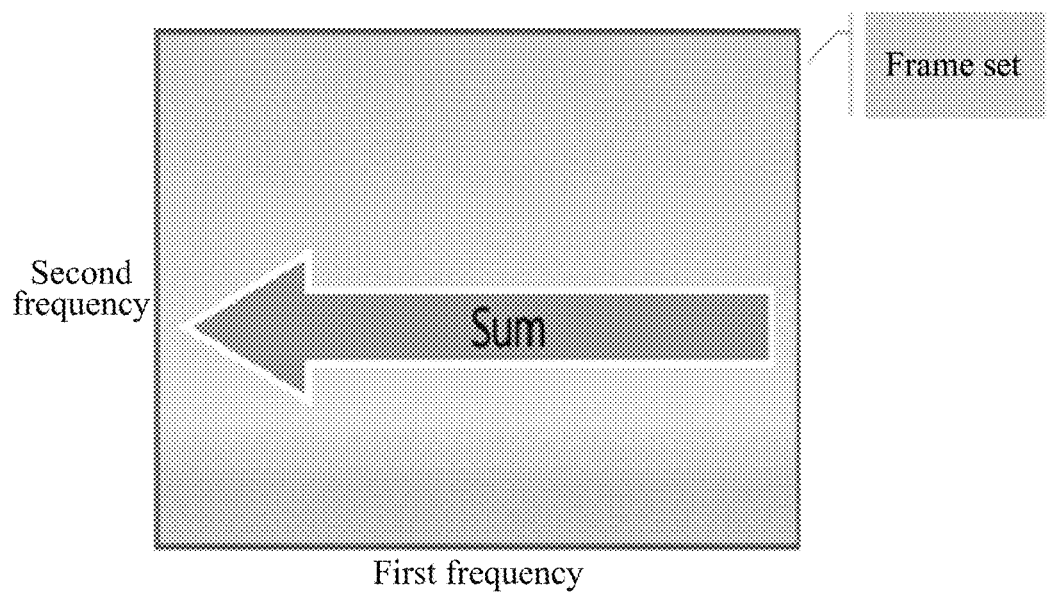
FIGS. 6A and 6B are diagrams illustrating a method of determining a heartbeat frequency of a target using a second magnitude spectrum determined by performing a frequency conversion of a first magnitude spectrum according to an example embodiment.
Figure 6B:
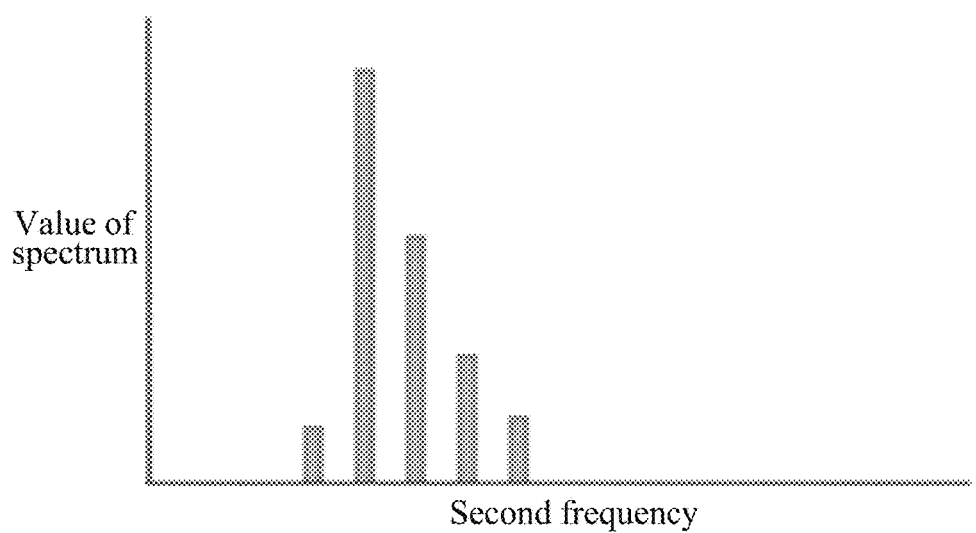

For example, the bio-information determination apparatus 100 may add up values of the second magnitude spectrum in a second frequency axis direction, as shown in FIG. 6A. As a result, the bio-information determination apparatus 100 may determine the third magnitude spectrum that is a one-dimensional (1D) magnitude spectrum for each second frequency as shown in FIG. 6B.

In operation 370, the bio-information determination apparatus 100 may determine a frequency corresponding to a peak in the third magnitude spectrum as the heartbeat frequency. The third magnitude spectrum may represent heartbeat frequencies of the target included in a frame set generated based on the reception radar signal collected using the reception antenna. For example, a second frequency having a highest value in the third magnitude spectrum may be a heartbeat frequency of the target to be measured.

As described above, the bio-information determination apparatus 100 may efficiently determine bio-information, for example, a heartbeat frequency, of a human using a UWB impulse radar. Unlike the related art, according to an example embodiment, a frequency conversion of a single frame may be performed, data may be converted to frequency domain data, and an additional process may be applied, and thus it is possible to efficiently extract bio-information of a target even though the target slightly moves or a distance between the target and a radar antenna changes.

In the related art, a method of determining a heartbeat frequency of a target using a reception radar signal is provided. However, it is difficult to determine an exact heartbeat frequency in response to a sudden and unintended movement of the target.

According to an embodiment, even though a distance between the target and the radar antenna changes due to a sudden and unintended movement of the target, the bio-information determination apparatus 100 may minimize an influence of a change in the distance, and may robustly determine the heartbeat frequency of the target.

According to example embodiments, a method of determining a heartbeat frequency of a target based on a frame set in the bio-information determination apparatus 100 in terms of each of a time domain and a frequency domain may be provided.

<Determination of Heartbeat Frequency of Target in Time Domain>

Figure 7:
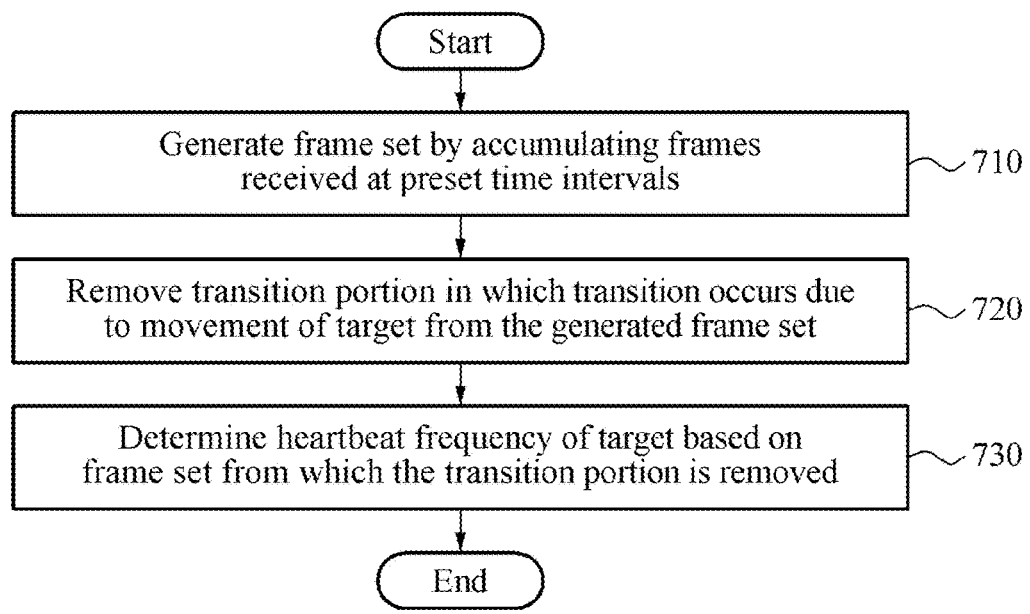
FIG. 7 is a flowchart illustrating another example of a method of determining a heartbeat frequency of a target using an impulse radar according to an example embodiment.

FIG. 7 is a flowchart illustrating another example of a method of determining a heartbeat frequency of a target using an impulse radar according to an example embodiment. The method of FIG. 7 may be performed by the bio-information determination apparatus 100 of FIG. 1.

Referring to FIG. 7, in operation 710, the bio-information determination apparatus 100 may generate a frame set by accumulating frames received at preset time intervals. The frames may be generated by overlapping of radar pulses reflected from a target of which a heart rate is to be measured.

The generated frame set may have a form in which a magnitude of a reception radar signal is expressed on a plane formed by a sampler index axis and a time axis. For example, the frame set may be represented as a data structure for a 2D matrix.

In operation 720, the bio-information determination apparatus may remove a transition portion in which a transition occurs due to a movement of the target from the generated frame set.

Figure 8A:
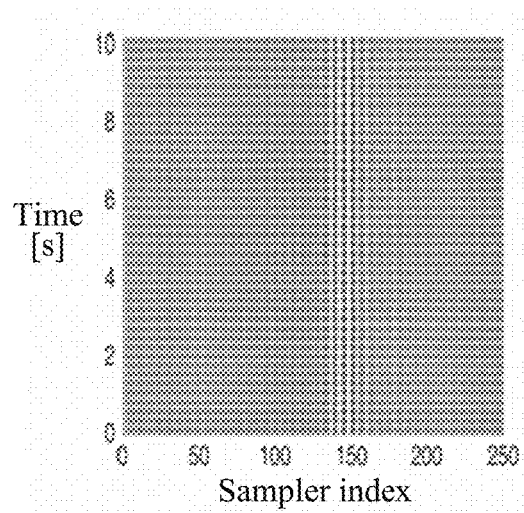
FIGS. 8A, 8B, 8C and 8D are diagrams illustrating a comparison between a frame set generated when a target moves and a frame set generated when the target does not move according to an example embodiment.
Figure 8B:
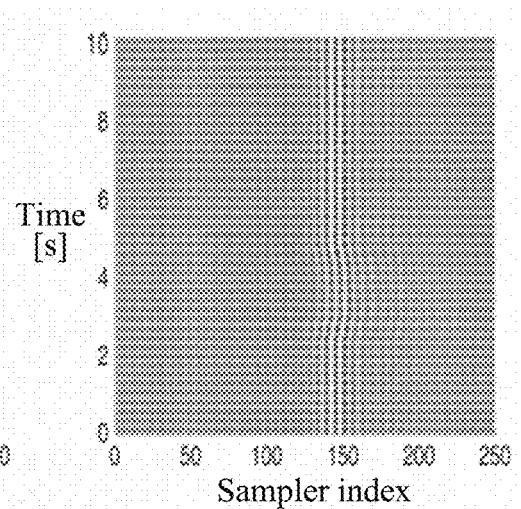

A frame set generated when the target moves, and a frame set generated when the target does not move may be compared with reference to FIGS. 8A, 8B, 8C and 8D. FIG. 8A illustrates a top view of the frame set generated when the target does not move, and FIG. 8B illustrates a top view of the frame set generated when the target moves. Referring to FIG. 8B, data is horizontally deviated in an interval of about 2.5 s to 4.7 s due to the movement of the target.

Figure 8C:
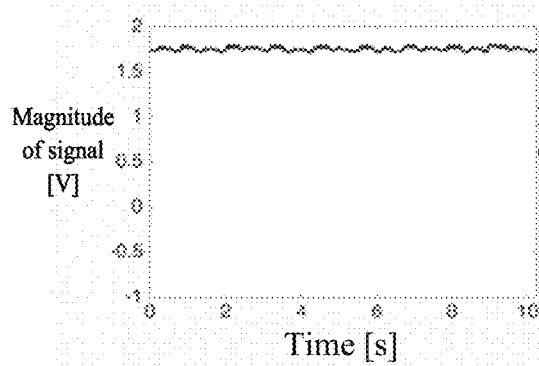
Figure 8D:
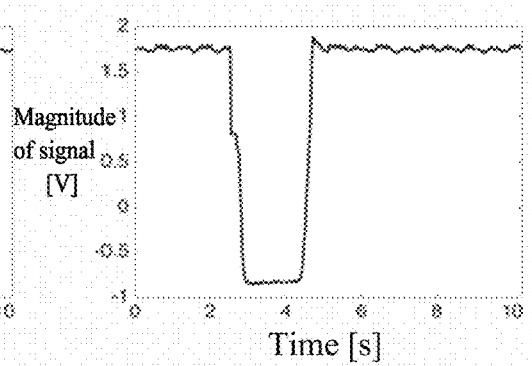

FIGS. 8C and 8D illustrate data in a time axis direction corresponding to a $142^{th}$ sampler in the frame sets of FIGS. 8A and 8B, respectively. A ripple shown in FIG. 8C may indicate that a phase of a reception radar signal fluctuates over time by a heartbeat of the target.

The bio-information determination apparatus 100 may process the above data in the time axis direction in the time domain or the frequency domain, to accurately extract the heartbeat frequency of the target. For example, data may be additionally processed when all frames included in the frame set are aligned along a time axis. However, when frames are not aligned as shown in FIG. 8B, data in the time axis direction may be collected and a transition portion may be present in a specific time interval as shown in FIG. 8D. Due to the transition portion, information about the heartbeat of the target may be distorted.

Thus, the bio-information determination apparatus 100 may minimize an influence of an unintended movement of the target, and may clarify an interval corresponding to a frame with the transition portion, to detect the heartbeat frequency of the target. A sampler index corresponding to a maximum peak in the frame set may reflect the movement of the target. A position in which the maximum peak occurs in the frame set may change based on a distance between the target and a radar antenna. For example, when the target 110 is located far away from the radar antenna, the sampler index may increase. Thus, it is possible to relatively accurately quantify the movement of the target by observing a position of a sampler index corresponding to the maximum peak in the frame set.

For example, the bio-information determination apparatus 100 may extract first sampler indices that each indicate a maximum peak of each of frames included in the frame set of FIG. 2C. The bio-information determination apparatus 100 may determine a sampler index corresponding to a largest number of maximum peaks among the first sampler indices as a second sampler index. For example, the 138$^{th}$ sampler may correspond to a largest number of maximum peaks as shown in FIG. 2C. In this example, the bio-information determination apparatus 100 may determine the second sampler index based on a histogram of the extracted first sampler indices.

Figure 9A:
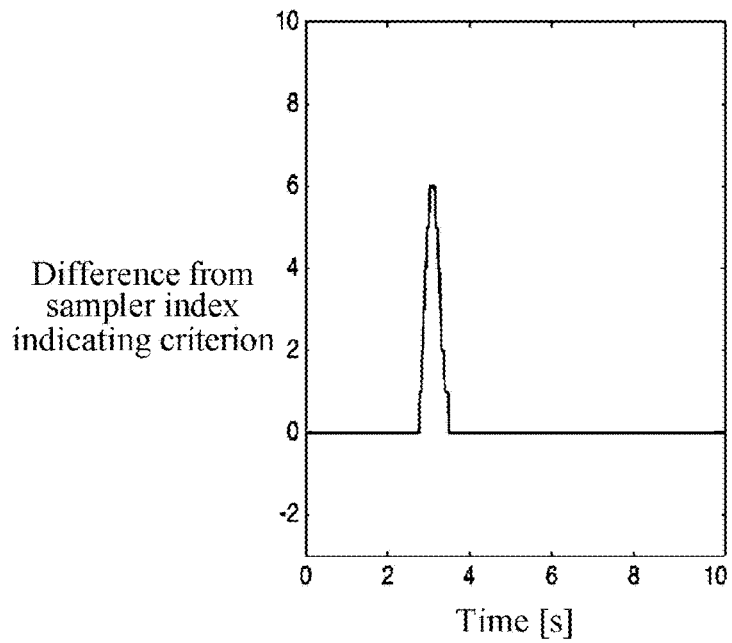
FIGS. 9A and 9B are diagrams illustrating examples of movement profiles according to an example embodiment.
Figure 9B:
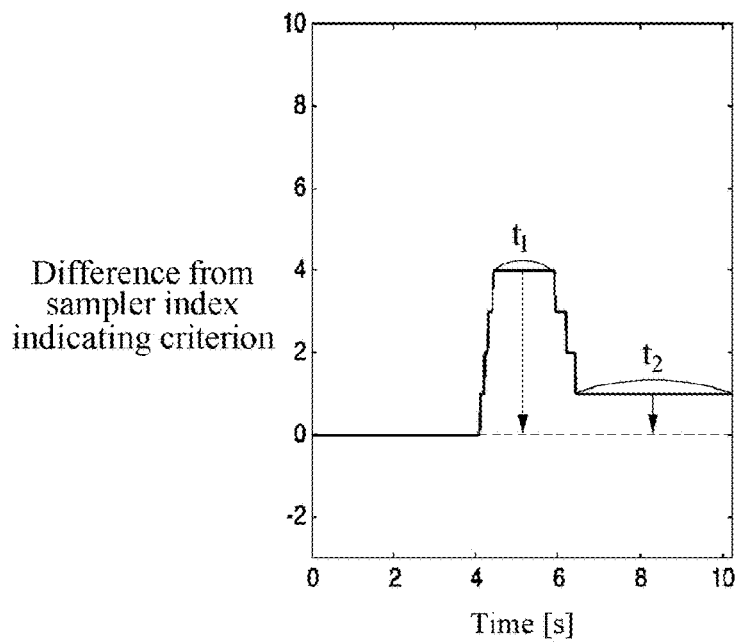

The bio-information determination apparatus 100 may generate a movement profile based on the movement of the target using a difference between a first sampler index and a second sampler index. For example, FIGS. 9A and 9B illustrate examples of movement profiles generated based on the difference between the first sampler index and the second sampler index. It may be found from FIG. 9A that the target moves in an interval of about 2.77 s to 3.51 s. Also, it may be found from FIG. 9B that the target moves in an interval of about 4.07 s to 4.41 s and an interval of about 5.91 s to 6.4 s.

The bio-information determination apparatus 100 may align frames included in the frame set based on the generated movement profile. For example, the bio-information determination apparatus 100 may control a maximum peak of each of the frames to match a maximum peak indicated by second sampler index based on the generated movement profile, and may remove a frame with a transition portion in which a transition occurs due to the movement of the target.

For example, because the target moves in the interval of about 2.77 s to 3.51 s as shown in FIG. 9A, all frames corresponding to the interval may be removed. In another example, as shown in FIG. 9B, all frames corresponding to the interval of about 4.07 s to 4.41 s and the interval of about 5.91 s to 6.4 s in which the target moves may be removed. However, frames corresponding to an interval $t_1$ of about 4.41 s to 5.91 s and an interval $t_2$ of about 6.4 s to 10.24 s may not need to be removed because the target does not move in the intervals $t_1$ and $t_2$.

Thus, the bio-information determination apparatus 100 may shift data of the frames corresponding to the intervals $t_1$ and $t_2$ by "4" and "1" in a sampler index axis direction so that a maximum peak of each of the frames corresponding to the intervals $t_1$ and $t_2$ may be aligned with a maximum peak indicated by the second sampler index.

The frame set reconstructed by the bio-information determination apparatus 100 as described above may be an incomplete frame set with empty data because frames with the transition portion are removed.

In operation 730, the bio-information determination apparatus may determine the heartbeat frequency of the target based on the frame set from which the frame with the transition portion is removed.

Because the frame set reconstructed in operation 720 is an incomplete frame set with empty data because a frame with the transition portion is removed, a statistical process may be required to measure an exact heartbeat frequency of the target.

The reconstructed frame set may be regarded as incomplete data that is uniformly sampled. Thus, to detect a weak frequency component in the incomplete data, the bio-information determination apparatus 100 may apply a Lomb-Scargle periodogram as a mathematical process to the incomplete data. The Lomb-Scargle periodogram may be a kind of deformed power spectral densities. The Lomb-Scargle periodogram may efficiently detect a periodic pattern and a result of the detecting may have a high precision, even though a periodic component is covered by noise.

A Lomb-Scargle normalized periodogram at a frequency f may be defined as shown in Equation 1, for a set of N data points $X_j = X(t_j)$ at times $t_j$ where $j=1, \ldots, N$.

$$P_X(f) = \frac{1}{2\sigma^2} \left\{ \frac{\left[\sum_j (X_j - \overline{X})\cos\omega(t_j - \tau)\right]^2}{\sum_j (\cos\omega(t_j - \tau))^2} + \frac{\left[\sum_j (X_j - \overline{X})\sin\omega(t_j - \tau)\right]^2}{\sum_j (\sin\omega(t_j - \tau))^2} \right\}$$ [Equation 1]

In Equation 1, $\omega=2\pi f$, and $\overline{X}$ and $\sigma^2$ denote a mean and variance of X(tj) and are represented by Equations 2 and 3 shown below, respectively.

$$\overline{X} = \frac{1}{N}\sum_{j=1}^{N} X_j$$ [Equation 2]

$$\sigma^2 = \frac{1}{N-1}\sum_{j=1}^{N}(X_j - \overline{X})^2$$ [Equation 3]

Also, a time offset τ may be defined by Equation 4 shown below.

$$\tan(2\omega\tau) = \frac{\sum_j \sin 2\omega t_j}{\sum_j \cos 2\omega t_j}$$ [Equation 4]

Figure 10:
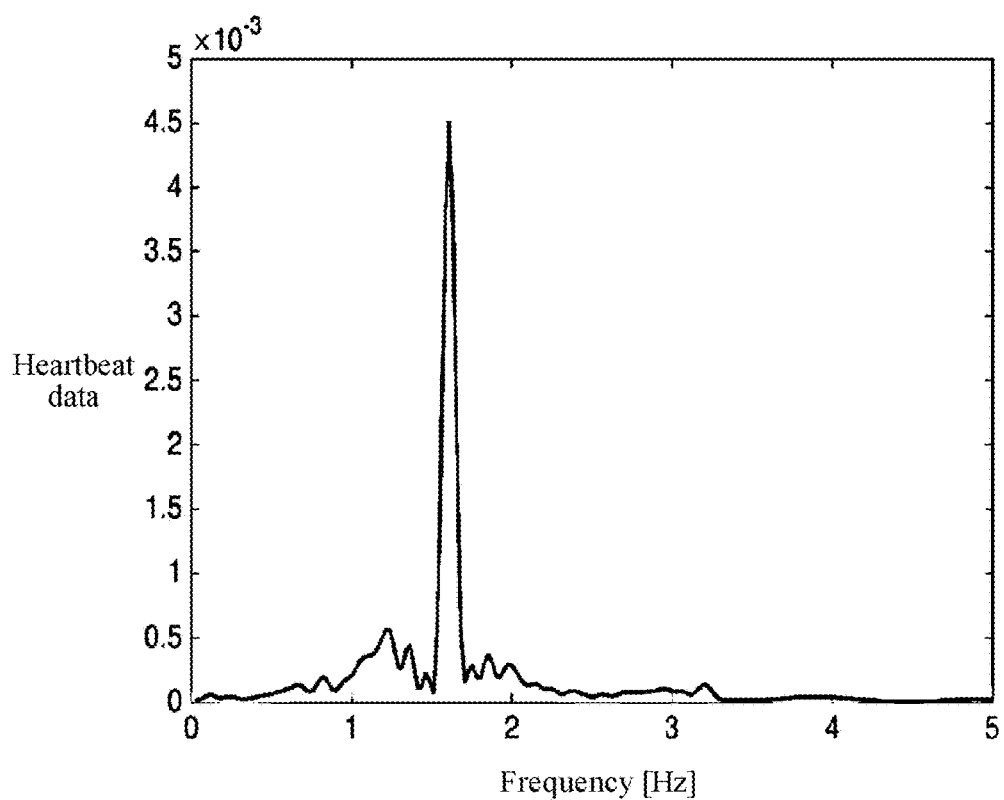
FIG. 10 is a diagram illustrating a result obtained by applying a periodogram according to an example embodiment.

The reconstructed frame set may include "512" pieces of data $X_j$ in a time axis direction corresponding to a sampler index indicting a maximum peak. The "512" pieces of data $X_j$ may include an empty interval corresponding to removed frames. Because a total number of pieces of data $X_j$ is "512," N may be set to "512." A periodogram may be calculated by applying N of "512" to Equation 1, to obtain a result shown in FIGS. 6A and 6B. As shown in FIG. 10, a frequency of about 1.61 Hz indicating a peak component may be a heartbeat frequency of the target acquired from the reconstructed frame set that is incomplete data.

<Determination of Heartbeat Frequency of Target in Frequency Domain>

The bio-information determination apparatus 100 may determine, based on a frame set, a heartbeat frequency of a target of which a heart rate is to be measured. The frame set may be generated by accumulating frames received at preset time intervals. The frames may be generated by overlapping of radar pulses reflected from the target. The bio-information determination apparatus 100 may process the frame set in a frequency domain instead of the above-described time domain, to determine the heartbeat frequency of the target.

For example, the bio-information determination apparatus 100 may extract first sampler indices that each indicate a maximum peak of each of frames included in the frame set of FIG. 2C. The bio-information determination apparatus 100 may determine a sampler index corresponding to a largest number of maximum peaks among the first sampler indices as a second sampler index. For example, the $138^{th}$ sampler may correspond to a largest number of maximum peaks as shown in FIG. 2C. In this example, the bio-information determination apparatus 100 may determine the second sampler index based on a histogram of the extracted first sampler indices.

The bio-information determination apparatus 100 may generate a movement profile based on a movement of the target using a difference between a first sampler index and a second sampler index. For example, FIGS. 9A and 9B illustrate examples of movement profiles generated based on the difference between the first sampler index and the second sampler index. It may be found from FIG. 9A that the target moves in an interval of about 2.77 s to 3.51 s. Also, it may be found from FIG. 9B that the target moves in an interval of about 4.07 s to 4.41 s and an interval of about 5.91 s to 6.4 s.

The bio-information determination apparatus 100 may determine a magnitude spectrum of the frame set corresponding to a frequency axis by performing a frequency conversion of frames included in the frame set in a sampler index axis direction. The determined magnitude spectrum may be used to minimize an influence of a movement of the target even thought the target moves.

The bio-information determination apparatus 100 may remove a portion corresponding to the movement of the target from the magnitude spectrum based on the movement profile. For example, because the target moves in the interval of about 2.77 s to 3.51 s as shown in FIG. 9A, the bio-information determination apparatus 100 may remove all frames corresponding to the interval from the magnitude spectrum. Similarly, because the target moves in the interval of about 4.07 s to 4.41 s and the interval of about 5.91 s to 6.4 s as shown in FIG. 9B, the bio-information determination apparatus 100 may remove all frames corresponding to the intervals from the magnitude spectrum.

The bio-information determination apparatus 100 may determine the heartbeat frequency of the target based on the magnitude spectrum from which the portion corresponding to the movement of the target is removed. For example, the bio-information determination apparatus 100 may apply a Lomb-Scargle periodogram as a mathematical process to data in a time axis direction with a frequency indicating a maximum peak in the magnitude spectrum from which the portion corresponding to the movement of the target is removed. The Lomb-Scargle periodogram may be a kind of deformed power spectral densities. The Lomb-Scargle periodogram may efficiently detect a periodic pattern and a result of the detecting may have a high precision, even though a periodic component is covered by noise.

Similarly to the time domain, the bio-information determination apparatus 100 may apply the Lomb-Scargle periodogram to the magnitude spectrum, to obtain a result of FIG. 10. In FIG. 10, a frequency of about 1.61 Hz indicating a peak component may be a heartbeat frequency of the target.

As described above, the bio-information determination apparatus 100 may efficiently determine bio-information, for example, a heartbeat frequency, of a human using a UWB impulse radar. For example, when a target suddenly and unintentionally moves, the bio-information determination apparatus 100 may remove a transition portion in which a transition occurs due to a movement of the target, and may apply the Lomb-Scargle periodogram to the removed transition portion, that is, incomplete data. Thus, it is possible to robustly and efficiently extract bio-information of the target with a higher accuracy.

Figure 11:
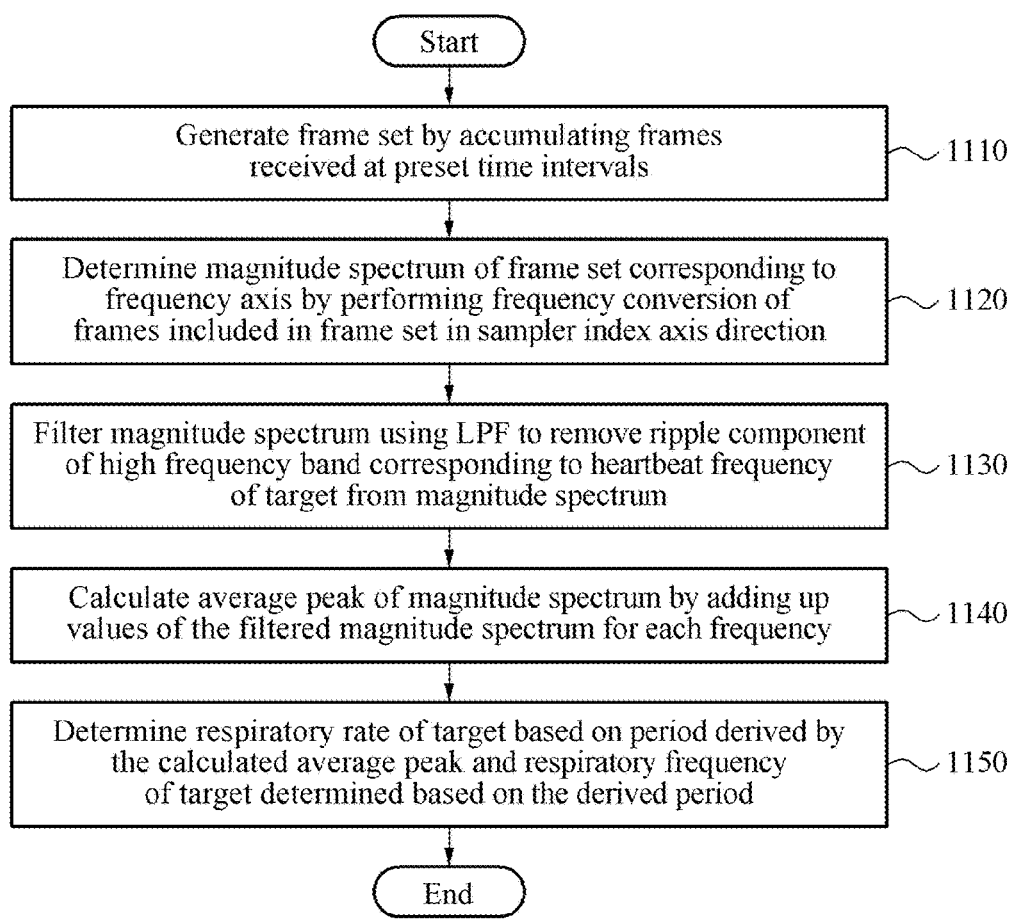
FIG. 11 is a flowchart illustrating a method of determining a respiratory rate of a target using an impulse radar according to an example embodiment.

FIG. 11 is a flowchart illustrating a method of determining a respiratory rate of a target using an impulse radar according to an example embodiment. The method of FIG. 11 may be performed by the bio-information determination apparatus 100 of FIG. 1.

The bio-information determination apparatus 100 may determine the respiratory rate of the target based on a reception radar signal. The reception radar signal may be collected using a reception antenna by reflecting a projected transmission radar signal from the target.

Referring to FIG. 11, in operation 1110, the bio-information determination apparatus 100 may generate a frame set by accumulating frames received at preset time intervals. The frames may be generated by overlapping of radar pulses reflected from a target of which a respiratory rate is to be measured.

The generated frame set may have a form in which a magnitude of a reception radar signal is expressed on a plane formed by a sampler index axis and a time axis. For example, the frame set may be represented as a data structure for a 2D matrix.

In operation 1120, the bio-information determination apparatus 100 may determine a magnitude spectrum of the frame set corresponding to a frequency axis by performing a frequency conversion of frames included in the frame set in a sampler index axis direction.

In the related art, a frame set is generated by accumulating a plurality of frames, and a frequency conversion is performed on data in a time axis direction corresponding to a specific sampler, for example, a sampler corresponding to a peak, to extract a respiratory frequency or a heartbeat frequency of a target. However, because a position of a sampler corresponding to a maximum peak occurring in each of frames included in the frame set fluctuates in response to a change in a distance between the target and a radar antenna, there is a need to attempt to perform a frequency conversion while continuing to track the fluctuation in the position, which may cause an inconvenience.

For example, a maximum peak occurring in each of the frames in the frame set may frequently fluctuate in the sampler index axis direction due to an influence by a respiration, and the like. Thus, it may be difficult to extract a respiratory frequency or a heartbeat frequency of a target based on data in the time axis direction corresponding to a specific sampler.

To overcome the above limitation, the bio-information determination apparatus 100 may perform a frequency conversion of each of frames included in a frame set of FIG. 4A in a sampler index axis direction as shown in FIG. 4B. As a result, a sampler index axis of the frame set may be converted to a first frequency axis, and a magnitude spectrum of the frame set corresponding to the first frequency axis may be determined. For example, the bio-information determination apparatus 100 may use an FFT to perform a frequency conversion of each of the frames.

The frequency conversion may be performed as described above, because even though the target slightly moves in the sampler index axis direction, an influence of a slight movement of the target may be reduced in the frequency domain.

In the magnitude spectrum determined by performing the frequency conversion of each of the frames, the reception radar signal may have a highest basic frequency, and an influence of a phase fluctuation in the reception radar signal due to a heartbeat or a respiration of the target may be represented in a form of a change over time in a size of a main lobe and a size of a side lobe for a basic frequency of the reception radar signal. The bio-information determination apparatus 100 may extract a heartbeat frequency of the target using the above fluctuation component of the magnitude spectrum.

In operation 1130, the bio-information determination apparatus 100 may filter the magnitude spectrum using a low-pass filter (LPF) to remove a ripple component of a high frequency band corresponding to the heartbeat frequency of the target from the magnitude spectrum.

The reception radar signal collected by the bio-information determination apparatus 100 using the reception antenna may include undesired noise that suddenly changes, or include information about a respiration of the target as well as information about a heartbeat of the target. Thus, to more accurately determine the respiratory rate of the target, the bio-information determination apparatus 100 may need to filter the magnitude spectrum to acquire the information about the respiration of the target.

To this end, the bio-information determination apparatus 100 may filter the magnitude spectrum in the time axis direction using the LPF. The bio-information determination apparatus 100 may remove a noise component and heartbeat data having a higher frequency than that of respiration data of the target, by filtering the magnitude spectrum using the LPF. In the magnitude spectrum filtered using the LPF, a fluctuation component caused by the respiration of the target may remain.

In operation 1140, the bio-information determination apparatus 100 may calculate an average peak of the magnitude spectrum by adding up values of the filtered magnitude spectrum for each frequency.

In operation 1150, the bio-information determination apparatus 100 may determine the respiratory rate based on a period derived by the calculated average peak and a respiratory frequency of the target determined based on the derived period.

For example, the bio-information determination apparatus 100 may calculate a respiratory period of the target as shown in Equation 5 below.

$$\text{Period}(T) = \text{average peak} \square 20 \text{ ms} \quad \text{[Equation 5]}$$

Also, the bio-information determination apparatus 100 may calculate a respiratory frequency of the target based on the respiratory period calculated in Equation 5, using Equation 6 shown below.

$$\text{Frequency (Hz)} = 1/\text{Period} \quad \text{[Equation 6]}$$

The bio-information determination apparatus 100 may determine the respiratory rate based on the calculated respiratory frequency, using Equation 7 shown below.

$$\text{RPM} = \text{Frequency} \square 60 \quad \text{[Equation 7]}$$

When the respiratory rate is determined based on the frame set as described above, the bio-information determination apparatus 100 may remove a frame that is first accumulated in the frame set, and may insert a last collected frame into the frame set, to reconstruct the frame set. The bio-information determination apparatus 100 may continue to determine the respiratory rate based on the reconstructed frame set.

FIGS. 12A, 12B, 12C, 12D, 12E and 12F illustrate a process of generating a frame set according to an example embodiment. Before the bio-information determination apparatus 100 of FIG. 1 determines a respiratory rate of a target, a frame set may be empty as shown in FIG. 12A. The bio-information determination apparatus 100 may collect frames using a reception antenna and may accumulate the frames in the frame set, as shown in FIG. 12B. When the frame set is completed by accumulating the frames as shown in FIG. 12C, the bio-information determination apparatus 100 may determine the respiratory rate of the target based on the frame set.

The bio-information determination apparatus 100 may remove a frame that is first accumulated from the frame set as shown in FIG. 12D, and may insert a last collected frame into the frame set as shown in FIG. 12E, to reconstruct the frame set as shown in FIG. 12F. The bio-information determination apparatus 100 may continue to determine the respiratory rate of the target based on the reconstructed frame set.

According to example embodiments, a frequency conversion of a single frame derived by radar pulses reflected from a target may be performed, data may be converted to a frequency domain data, and an additional process may be applied. Thus, it is possible to efficiently extract bio-information of the target even though a distance between the target and a radar antenna changes or the target slightly moves.

The units described herein may be implemented using hardware components, software components, and/or a combination thereof. For example, the units and components described herein may be implemented using one or more general-purpose or special purpose computers, such as, for example, a processor, a controller and an arithmetic logic unit (ALU), a digital signal processor, a microcomputer, a field programmable gate array (FPGA), a programmable logic unit (PLU), a microprocessor, or any other device capable of responding to and executing instructions in a defined manner. A processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of determining bio-information of a target, the method comprising:
   generating a frame set by accumulating frames received at preset time intervals, the frames being generated by overlapping of radar pulses reflected from a target of which a heart rate is to be measured;
   determining a first magnitude spectrum of the frame set corresponding to a first frequency axis by performing a frequency conversion of frames included in the frame set in a sampler index axis direction;
   determining a second magnitude spectrum of the frame set corresponding to the first frequency axis and a second frequency axis by performing a frequency conversion of the first magnitude spectrum in a time axis direction;
   determining a third magnitude spectrum of the frame set by adding up values of the second magnitude spectrum in a second frequency axis direction; and
   determining a frequency indicating a peak in the third magnitude spectrum as a heartbeat frequency of the target.

2. The method of claim 1, further comprising:
   filtering the first magnitude spectrum in the time axis direction using a band-pass filter (BPF) with a frequency band corresponding to the heartbeat frequency; and
   applying a window function corresponding to a data length in the time axis direction to the filtered first magnitude spectrum,
   wherein the determining of the second magnitude spectrum comprises determining the second magnitude spectrum by performing the frequency conversion of the first magnitude spectrum, to which the window function is applied, in the time axis direction.

* * * * *

UNITED STATES PATENT AND TRADEMARK OFFICE
CERTIFICATE OF CORRECTION

| | | |
|---|---|---|
| PATENT NO. | : 10,383,545 B2 | Page 1 of 1 |
| APPLICATION NO. | : 15/362873 | |
| DATED | : August 20, 2019 | |
| INVENTOR(S) | : Cho et al. | |

It is certified that error appears in the above-identified patent and that said Letters Patent is hereby corrected as shown below:

On the Title Page

Item (30) should read:
--(30) Foreign Application Priority Data
Sep. 29, 2016     (KR) ........................ 10-2016-0125691
Oct. 4, 2016       (KR) ........................ 10-2016-0127798
Oct. 4, 2016       (KR) ........................ 10-2016-0127819--

Signed and Sealed this
Twenty-eighth Day of January, 2020

Andrei Iancu
*Director of the United States Patent and Trademark Office*